United States Patent
Ye et al.

(10) Patent No.: US 12,385,015 B2
(45) Date of Patent: Aug. 12, 2025

(54) METHOD FOR CONSTRUCTING gE PROTEIN-DELETED PSEUDORABIES VIRUS STRAIN USING ADENINE BASE EDITOR AND USE THEREOF

(71) Applicant: JIANGXI AGRICULTURAL UNIVERSITY, Nanchang (CN)

(72) Inventors: Yu Ye, Nanchang (CN); Peixia Wang, Nanchang (CN); Yuxin Tang, Nanchang (CN); Chuan Zeng, Nanchang (CN); Jun Gu, Nanchang (CN); Jinyan Shen, Nanchang (CN); Yiwen Duan, Nanchang (CN); Yuwei Bai, Nanchang (CN); Dongyan Huang, Nanchang (CN); Deping Song, Nanchang (CN)

(73) Assignee: JIANGXI AGRICULTURAL UNIVERSITY, Nanchang (CN)

( * ) Notice: Subject to any disclaimer, the term of this patent is extended or adjusted under 35 U.S.C. 154(b) by 0 days.

(21) Appl. No.: 18/903,289

(22) Filed: Oct. 1, 2024

(65) Prior Publication Data
US 2025/0136951 A1    May 1, 2025

(30) Foreign Application Priority Data
Oct. 25, 2023   (CN) .......................... 202311385572.1

(51) Int. Cl.
C12N 7/04        (2006.01)
C12N 15/10       (2006.01)

(52) U.S. Cl.
CPC ......... *C12N 7/045* (2013.01); *C12N 15/1031* (2013.01); *C12N 2710/16721* (2013.01)

(58) Field of Classification Search
CPC ................ C12N 7/045; C12N 15/1031; C12N 2710/16721
See application file for complete search history.

(56) References Cited

FOREIGN PATENT DOCUMENTS

| CN | 104928261 A | 9/2015 |
| CN | 109706185 A | 5/2019 |
| CN | 109706185 B | * 7/2021 |

OTHER PUBLICATIONS

Zhai et al (2019). Genome Characteristics and Evolution of Pseudorabies Virus Strains in Eastern China from 2017 to 2019. Virol Sin. Dec. 2019;34(6):601-609. (Year: 2019).*
Wang et al (2020). Efficient gene silencing by Adenine Base Editor-mediated start codon mutation. Molecular Therapy, 28(2):431-440. (Year: 2020).*
Yao et al (2021). Recombinant Pseudorabies Virus with TK/gE gene deletion and Flt3L co-expression enhances the innate and adaptive immune response via activating dendritic cells. Viruses,2021, 13(4), 691. (Year: 2021).*
Ming, J. et al., "Rapid Construction of the PRVgE Gene Deletion Virus Based on CRISPR / Cas 9 Technology," China Academic Journal Electronic Publishing House, v. 37, (2020), 20 pgs.
1st Office Action dated Dec. 6, 2023 for CN Appn. No. 202311385572. 1, 11 pgs.
2nd Office Action dated Dec. 22, 2023 for CN Appn. No. 202311385572. 1, 11 pgs.

* cited by examiner

*Primary Examiner* — Janet L Andres
*Assistant Examiner* — Samadhan Jaising Jadhao
(74) *Attorney, Agent, or Firm* — Brooks Kushman P.C.

(57) ABSTRACT

Provided is a method for constructing a gE protein-deleted pseudorabies virus (PRV) strain using an adenine base editor (ABE) and use thereof. The method includes: designing an sgRNA sequence using the ABE with a start codon of the gE gene in a PRV as a target site, ligating an enzyme-digested fragment to a double-stranded DNA fragment with sticky ends to obtain a ligation product; and transforming the ligation product into a competent cell to allow plate screening and culture, selecting a resulting positive bacterial strain to allow expanded culture, and extracting a plasmid from a resulting positive bacterial solution; and transferring the plasmid into a target cell to allow the transfection for 24 h, collecting a resulting virus liquid, and centrifuging the virus liquid to collect a resulting supernatant.

4 Claims, 3 Drawing Sheets

Specification includes a Sequence Listing.

METHOD FOR CONSTRUCTING gE PROTEIN-DELETED PSEUDORABIES VIRUS STRAIN USING ADENINE BASE EDITOR AND USE THEREOF

CROSS-REFERENCE TO RELATED APPLICATION

This patent application claims the benefit and priority of Chinese Patent Application No. 202311385572.1 filed with the China National Intellectual Property Administration on Oct. 25, 2023, the disclosure of which is incorporated by reference herein in its entirety as part of the present application.

REFERENCE TO SEQUENCE LISTING

A computer readable XML file entitled "HLP20240100365_sequence_listing_updated which was created on Feb. 10, 2025", with a file size of about 27,800 bytes, contains the sequence listing for this application, has been filed with this application, and is hereby incorporated by reference in its entirety.

TECHNICAL FIELD

The present disclosure relates to the field of biotechnology, specifically to a method for constructing a gE protein-deleted pseudorabies virus (PRV) strain using an adenine base editor (ABE) and use thereof.

BACKGROUND

Pseudorabies is a higEly contagious, septicemic, and severe infectious disease caused by pseudorabies virus (PRV) infection. Pigs of all ages are susceptible to the PRV. Pregnant sows infected with PRV can cause abortion, stillbirth, mummification, or weak fetuses. Infection of piglets with PRV can cause higE fever, neurological symptoms, and dyspnea, while newborn piglets mostly show neurological symptoms after infection. After breeding pigs are infected with the PRV, breeding pigs may be infertile, sows may not be in estrus to cause difficulty in breeding, and boar testicles may be swollen and atrophied, losing the ability to breed. PRV is a double-stranded DNA virus with a full genome length of about 150 kb and an average G+C content of up to 74%. The PRV consists of a unique long segment (UL), a unique short segment (US), terminal repeats (TRs) on both sides, and internal repeats (IRs). Studies have found that gE is the main virulence gene but is not required for virus proliferation. Therefore, silencing the virulence gene gE can reduce the virulence of virus without affecting the immunogenicity, such that a resulting attenuated virus strain can be used as a vaccine candidate strain for the control and eradication of pseudorabies.

Early gene editing technologies generally adopt a principle of DNA homologous recombination, including zinc-finger nucleases (ZFNs) and transcription activator-like effector nucleases (TALENs), but their development was limited due to shortcomings such as complex design, low knockout efficiency, serious off-target, higE cost, and poor operability. Since its discovery, the clustered regularly interspaced short palindromic repeats/CRISPR-associated protein 9 (CRISPR/Cas9) system has become the most popular genetic modification tool due to its efficiency, convenience, and wide range of applications, achieving successful gene knockout. However, similar to technologies such as ZFNs and TALENs, gene editing by CRISPR/Cas9 relies on the generation of DNA double-strand breaks, triggering repair and resulting in unexpected base mutations or off-target cuts and structural variations in the genome. To overcome this shortcoming, the emergence of single base editing technology brings hope for achieving precise and efficient base conversion.

The single base editing technology is to fuse a modified Cas protein with no nuclease cleavage activity or single-strand nicking activity and a deaminase, and accurately anchor a resulting fused deaminase to a target site with sgRNA to allow base deamination, thereby achieving precise editing of single bases. This technology greatly improves the accuracy and efficiency of base editing. tRNA adenylate deaminase (TadA) is fused with nCas9 to develop a novel single-base conversion system (namely an adenine base editor, ABE) that can accurately convert adenine into guanine. After 7 rounds of transformation, a higEer-efficiency ABE version ABE7.10 is selected, with its effective editing window at positions 4 to 7 of the sgRNA. A deaminase component of the ABE7.10 continues to improve, resulting in a current version of the ABE with a higEer editing efficiency: ABE8e. Compared with ABE7.10, the ABE8e contains 8 additional mutations, which can increase the activity 590 times, and can greatly improve the editing efficiency when being paired with various Cas9 or Cas12 homologues. Since the development of ABE tools, studies have confirmed that the single base editors can work efficiently in multiple species, such as bacteria, plants, and mammals, but their application in viral genome modification has not yet been reported.

Existing ZFNs and TALENs are time-consuming, labor-intensive, and expensive to use; while the CRISPR/Cas9 shows low efficiency, difficulty in screening, and the generation of structural variations due to genome breaks. AlthougE other base editing tools can achieve silencing, more bystander effects are generated and some areas cannot be edited due to PAM restrictions.

SUMMARY

In order to solve at least one of the technical problems existing in the prior art, a purpose of the present disclosure is to provide a method for constructing a gE protein-deleted PRV strain using an ABE and use thereof.

The technical solutions of the present disclosure are as follows:

The present disclosure provides a gE protein-deleted PRV strain, where the gE protein-deleted PRV strain is deposited in the China Center for Type Culture Collection (CCTCC) on Jun. 30, 2023, in the Wuhan University, Wuhan City, Hubei Province, China, with a deposit number of CCTCC NO: V202323; and the gE protein-deleted PRV strain is named as porcine pseudorabies virus PRV-AgE-ABE and constructed using an ABE.

Preferably, a base at position 2 of a start codon in the gE gene of wild-type PRV is mutated from T to C, and a resulting mutated gE gene is set forth in SEQ ID NO: 1.

The present disclosure further provides a method for constructing the gE protein-deleted PRV strain using an ABE, including the following steps:

(1), constructing an sgRNA backbone plasmid:
designing an sgRNA sequence using the ABE with a start codon of the gE gene in a PRV as a target site, synthesizing a single-stranded oligonucleotide according to the sgRNA sequence, annealing the single-stranded oligonucleotide to obtain a double-stranded DNA fragment with sticky ends, digesting a pU6-sgRNA-Puro-2A-EGFP vector with a restriction endonuclease and recovering a resulting enzyme-digested fragment, and then ligating the enzyme-digested fragment to the double-stranded DNA fragment with sticky ends to obtain a ligation product, namely an sgRNA expression vector; and transforming the ligation product into a competent cell to allow plate screening and culture, selecting a resulting positive bacterial strain to allow expanded culture, and extracting a plasmid from a resulting positive bacterial solution; and (2), transfection of the plasmid:

transferring the plasmid into a Vero81 cell to allow the transfection, collecting a resulting virus liquid, and centrifuging the virus liquid to collect a resulting supernatant.

Preferably, the sgRNA sequence is set forth in SEQ ID NO: 2.

Preferably, the restriction endonuclease is a BbsI enzyme.

Preferably, the Vero81 cell is cultured in a fetal bovine serum (FBS)-containing medium to a logarithmic growth phase before the transfection is conducted.

Preferably, the single-stranded oligonucleotide has a sequence as follows:

```
NG-ABE8e-gE-F:
                                  (SEQ ID NO: 3)
CACCGGCCGCATGGTCTCAACCCC;

NG-ABE8e-gE-R:
                                  (SEQ ID NO: 4)
AAACGGGGTTGAGACCATGCGGCC.
```

Preferably, NG-ABE8e is a plasmid expressing the nCas9 protein.

The present disclosure further provides a gE protein-deleted PRV strain prepared by the method.

The present disclosure further provides use of the gE protein-deleted PRV strain in preparation of a pseudorabies vaccine.

The present disclosure has the following beneficial effects:

In the present disclosure, the ABE is used to modify the start codon ATG with reference to FIG. 1, and can block protein translation from the source. The method can be used as a new gene silencing technology to supplement the limitations of editing sites in the prior art. In the gE protein-deleted PRV strain prepared using this method, there is no structural variation in the PRV strain, and the termination of gE expression can be achieved by simply modifying a small amount of A or T bases in ATG. Moreover, a potential regulatory role of the gene sequence is minimally affected.

In the present disclosure, the method has higE efficiency and small changes to viral genes, does not cause large structural variations in the viral genome, and is low in cost.

In the present disclosure, the gE protein-deleted PRV strain is deposited in the CCTCC on Jun. 30, 2023, in the Wuhan University, Wuhan City, Hubei Province, China, with a deposit number of CCTCC NO: V202323; and the gE protein-deleted PRV strain is named: porcine pseudorabies virus PRV-AgE-ABE.

DETAILED DESCRIPTION OF THE EMBODIMENTS

Figure 1:
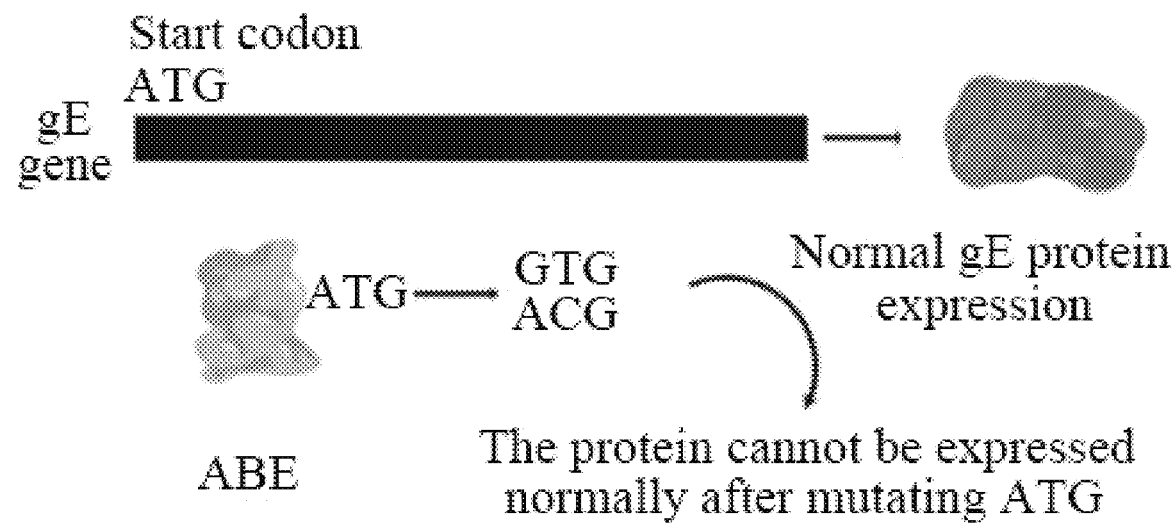
FIG. 1 shows a principle flow chart for constructing the gE protein-deleted PRV strain in the present disclosure.

The technical solutions of the present disclosure will be further described in detail below in conjunction with specific examples.

All experimental materials used in the following examples are purchased from conventional biochemical reagent companies, unless otherwise specified.

NG-ABE8e vector: Addgene, product number: 138491;
in the NG-ABE8e vector, a CMV promoter drives the expression of related proteins;
an ABE NG-ABE8e expresses adenine deaminase for point mutations; and
an sgRNA backbone plasmid includes a binding region that binds the target sequence and a binding region that binds the Cas9 protein.

I. Construction of an sgRNA backbone plasmid In this example, a start codon of the gE gene was selected as a target site; An sgRNA with a recognition sequence was designed as follows:

```
NG-ABE8e-gE:
                                  (SEQ ID NO: 2)
GGCCGCATGGTCTCAACCCC;
```

A single-stranded oligonucleotide was synthesized according to the designed sequence. A sequence of the single-stranded oligonucleotide was as follows:

```
NG-ABE8e-gE-F:
                                  (SEQ ID NO: 3)
CACCGGCCGCATGGTCTCAACCCC;

NG-ABE8e-gE-R:
                                  (SEQ ID NO: 4)
AAACGGGGTTGAGACCATGCGGCC;
``` the NG-ABE8e-gE-F and NG-ABE8e-gE-R were annealed to obtain a double-stranded DNA fragment with sticky ends;

a pU6-sgRNA-Puro-2A-EGFP vector was digested with a BbsI enzyme, and a resulting fragment was recovered and then ligated to the double-stranded DNA fragment with sticky ends to obtain an sgRNA expression vector; and an ABE NG-ABE8e included Cas9 (N), which in this example could specifically be a plasmid expressing the nCas9 protein.

The pU6-sgRNA-Puro-2A-EGFP vector consists of pU6, sgRNA, Puro, 2A, and EGFP" and has the sequence set forth in SEQ ID NO: 11. The pU6-sgRNA-Puro-2A-EGFP vector is commercially available. In the name of pU6-sgRNA-Puro-2A-EGFP vector, p represents plasmid, U6 represents U6 promoter (SEQ ID NO: 12), sgRNA represents sgRNA scaffold (SEQ ID NO: 13), EGFP represents enhanced green fluorescent protein (SEQ ID NO: 14), 2A represents linker 2A peptide (SEQ ID NO: 15), and Puro represents puromycin (SEQ ID NO: 16).

(1) Construction of a Double-Stranded sgRNA

The following table showed a phosphorylation annealing system;

TABLE 1

Phosphorylation annealing system

| Reagent | System (μL) |
| --- | --- |
| Forward single strand (100 μM) | 1 |
| Reverse single strand (100 μM) | 1 |
| 10 × T4 DNA ligation buffer (NEB) | 1 |
| T4 PNK (NEB) | 1 |
| Double distilled water | Supplementing to 10 μL |

A gradient annealing program was shown in Table 2:

TABLE 2

Gradient annealing program

| Temperature | Time | Gradient |
| --- | --- | --- |
| 37° C. | 30 min | — |
| 95° C. | 5 min | — |
| 95-85° C. | 1 min | −5° C. |
| 85-75° C. | 1 min | −5° C. |
| 75-65° C. | 1 min | −5° C. |
| 65-55° C. | 1 min | −5° C. |
| 55-45° C. | 1 min | −5° C. |
| 45-35° C. | 1 min | −5° C. |
| 35-25° C. | 1 min | −5° C. |
| 4° C. | Hold | — |

(2) Construction and Expression of a Linearized Backbone Vector Plasmid

The table below (Table 3) showed an enzyme digestion system of PX459 vector.

TABLE 3

Enzyme digestion system of PX459 vector

| Reagent | Volume (μL) |
| --- | --- |
| 10 × NEB | 5 |
| Restriction endonuclease BbsI | 1 |
| PX459 vector (2 μg) | 3.5 |
| Double distilled water | 40.5 |
| Total | 50 |

Reaction procedure: the enzyme digestion system was placed in a 37° C. water bath for 2 h to obtain an enzyme digestion product.

The enzyme digestion product was detected by agarose gel electrophoresis, and a target band was recovered from a gel the after electrophoresis.

(3) Construction of a Backbone Plasmid Expressing sgRNA

The following table (Table 4) showed a ligation reaction system.

TABLE 4

Ligation reaction system

| Reagent | Volume (μL) |
| --- | --- |
| 10 × T4 DNA ligation buffer | 1 |
| T4 DNA ligase (NEB) | 1 |
| Linearized PX459 vector (50 ng) | 2 |
| 200-fold-diluted gE-sgRNA annealing product | 1 |
| Double distilled water | 5 |
| Total | 10 |

The ligation product was transformed into Top 10 competent cells by conventional methods. An appropriate amount of resulting bacterial solution was applied onto an LB plate containing ampicillin. After liquid on the surface of the plate evaporated, the plate was put upside down in a 37° C. incubator to allow overnigEt culture for 16 h to 18 h, and the transformation was observed. 5 single-clonal colonies were selected, cultured with shaking and sequenced. The positive colonies with correct sequencing were further selected to allow expanded culture, and endotoxic-free plasmids for cell transfection were extracted and then stored at −20° C.

II. Plasmid Transfection (1) One day before transfection, the well-growing Vero81 cells were digested with trypsin, $1\times10^6$ digested cells were transferred to a six-well plate, and added with 2 mL of DMEM medium containing 10% (v/v) FBS (purchased from Gibco), and cultured to logarithmic growth phase at 37° C. and 5% (v/v) $CO_2$.

(2) Cell transfection was conducted according to the official instructions of Lipofectamine3000, where a total amount of transfected DNA was 3 μg, including 1 μg each of viral genomic DNA, NG-ABE8e plasmid, and sgRNA expression vector plasmid.

(3) 24 h after transfection, the presence or absence of PRV characteristic lesions was observed under a microscope. After lesions were observed, the six-well plate was frozen and thawed three times at −80° C. to room temperature, the collected virus liquid was centrifuged at 8,000 rpm for 5 min, and a portion of the collected supernatant was used to extract genes for sequencing. The detection primers were synthesized according to Table 5, and the target genes were amplified using the corresponding primers. The procedures were shown in Table 6. During amplification, a temperature with the lowest Tm value in the primer pair was used as an annealing temperature of the PCR reaction, and the extension time was set to 7 s according to the characteristics of the polymerase used. The results of PCR products were analyzed by agarose gel electrophoresis, and the successfully identified target fragments were cut out and sent to ShangEai Sangon Biotech Co., Ltd. for sequencing.

TABLE 5

Synthetic sequences of PCR detection primers

| Name | Sequence (5'-3') | Target fragment size |
| --- | --- | --- |
| gE-T-F | TGATCTTCCTGGGCGGGAT (SEQ ID NO: 5) | 584 bp |
| gE-T-R | TCGGACACGTTCACCAGAT (SEQ ID NO: 6) | |

TABLE 6

PCR program

| | Temperature (° C.) | Time | |
|---|---|---|---|
| Initial denaturation | 98 | 30 s | |
| Denaturation | 98 | 10 s | 35 cycles |
| Annealing | 57 | 5 s | 35 cycles |
| Extension | 72 | 7 s | 35 cycles |
| Total extension | 72 | 1 min | |
| Short-term storage | 4 | 30 min | |

Figure 2:
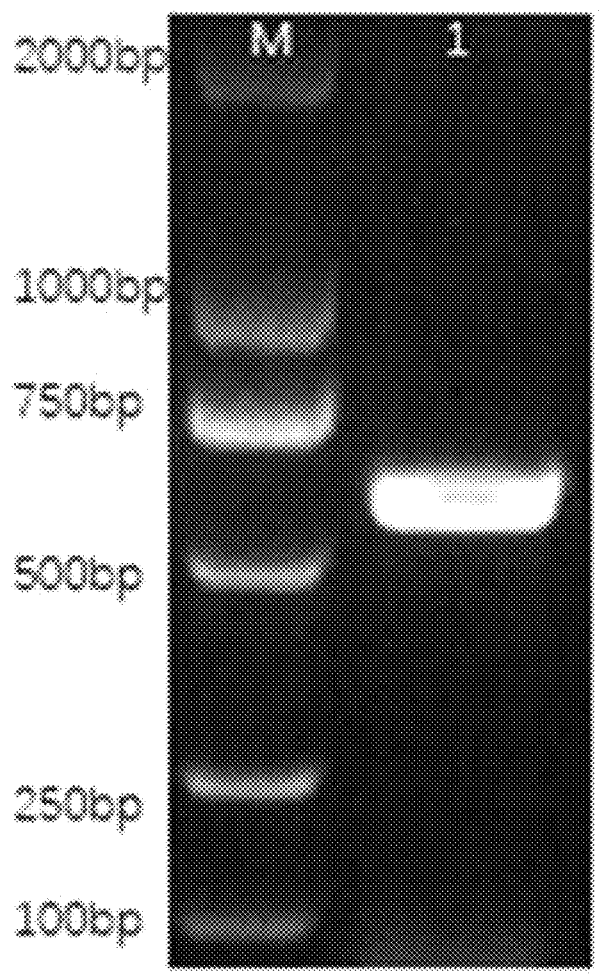
FIG. 2 shows a nucleic acid electrophoresis gel image of the PCR product after mutation of a first start codon of the gE gene in the present disclosure; where lane M represents a DL2000 Marker, and lane 1 represents a target band for sequencing.

Results: PCR detection was conducted using gE-T-F and gE-T-R as upstream and downstream primers, and a target band of the expected size was obtained. The results of gel electrophoresis of PCR products are shown in FIG. 2.

(4) After successful sequencing, the sequencing results were compared with the wild-type PRV gene to obtain detailed mutation information.

Figure 3:
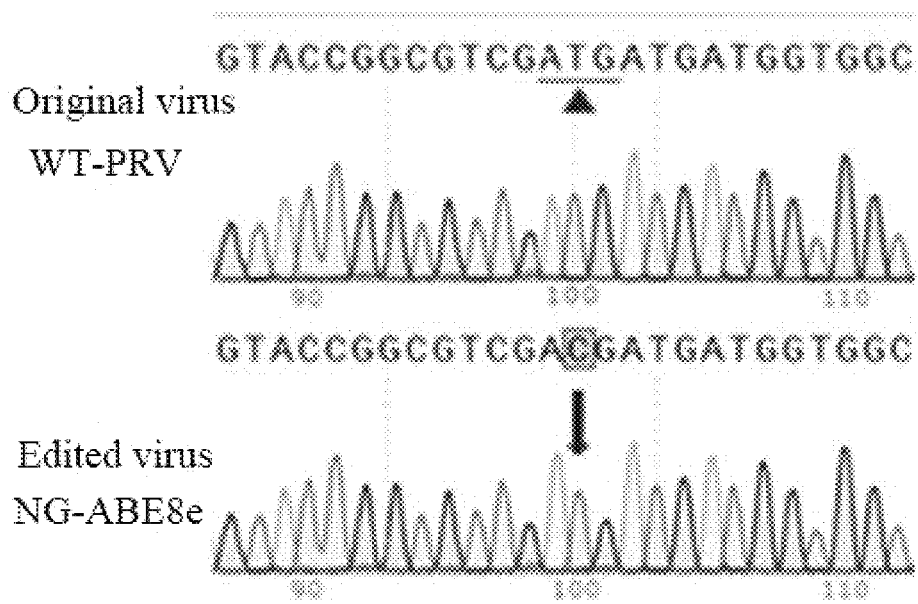
FIG. 3 shows a sequencing map of the viral gE gene edited in the present disclosure; where the underline represents an expected mutant gene, the triangle represents a mutation site, and the arrow represents a result after mutation.

The sequencing results are shown in FIG. 3. The comparison results showed that base T was successfully mutated into base C, with only a small amount of T remaining. A mutated gE gene was set forth in SEQ ID NO: 1.

The obtained gE protein-deleted PRV strain was deposited in the CCTCC on Jun. 30, 2023, with a deposit number of CCTCC NO: V202323; and the gE protein-deleted PRV strain was named: porcine pseudorabies virus PRV-AgE-ABE.

III. Plaque Purification of Mutant Strain (1) The virus supernatant was serially diluted 10 to $10^6$ times in a ten-fold ratio. The different dilutions of virus liquids were inoculated separately into a 12-well plate filled with Vero81 monolayer cells, with 200 µL in each well, the cells were incubated for 2 h with the cell plate shaken every half hour. The virus liquid was discarded, and cell surface was washed 3 times with a serum-free DMEM medium for later use.

(2) The autoclaved 2% (w/v) low melting point agarose was dissolved by microwave heating, cooled to about 37° C., mixed thorougEly with an equal volume of 2×DMEM medium containing 4% FBS, quickly added into the 12-well plate, with 1 mL to each well, and placed at room temperature for about 0.5 h. After the medium solidified naturally, the plate was put upside down in a carbon dioxide cell incubator for culture.

(3) After 48 h of incubation, cell lesions and plaque formation were observed. Multiple single plaques were randomly selected with a 10 µL pipette tip in the low dilution wells, blown into 200 µL of DMEM medium, mixed well and inoculated with Vero81 cells in a 24-well plate to allow expanded culture.

(4) After a large number of lesions appeared on the cells, the virus liquid was collected, the viral DNA was extracted, the target fragment was amplified using primers, followed by proceeding to the next round of purification based on the corresponding sequencing results.

(5) After purification, the virus was passed througE 10 consecutive passages, sequencing was conducted to verify the stability of the mutant gene, and the virus liquid was collected.

Figure 4:
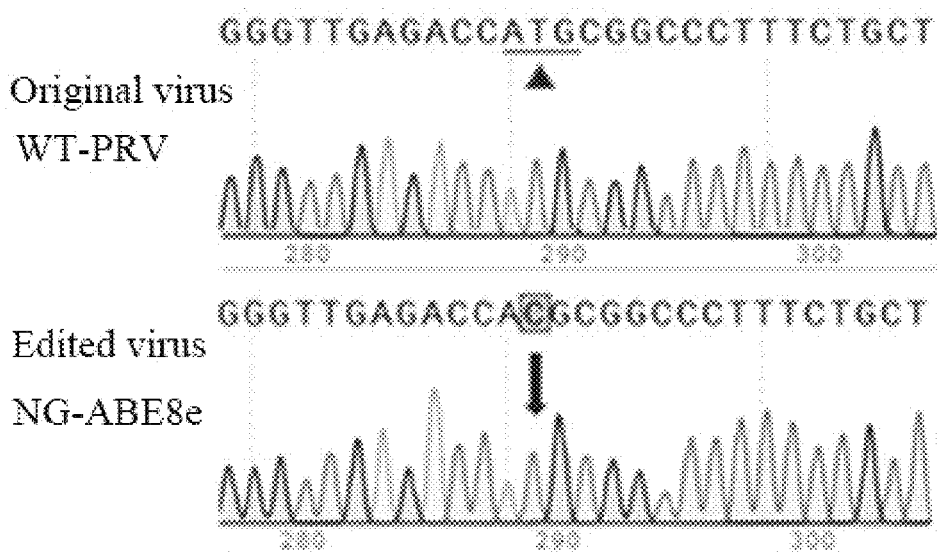
FIG. 4 shows a sequencing profile of PRV-AgE after 10 passages.

Results: the PRV-AgE-ABE gene sequencing results after 10 passages were shown in FIG. 4. Based on the sequencing results, it was preliminarily determined that the inheritance of single-base mutations in the gE gene was relatively stable.

IV. Analysis of Expression of Viral Proteins Caused by Gene Silencing (1) Whether the expression of target gene was silenced detected by Western blot The purified virus was internalized into Vero81 cells, and the viral protein was collected 24 h after inoculation, and Western blot was conducted to detect the expression of the gE gene.

Figure 5:
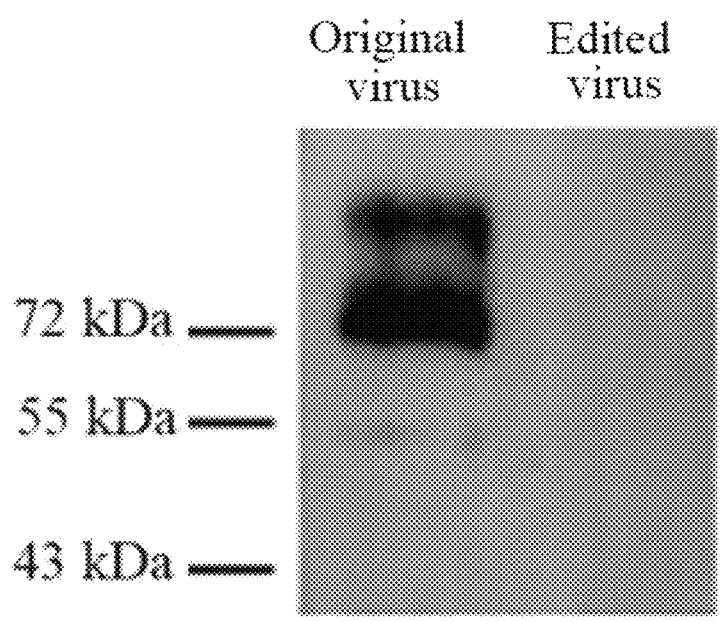
FIG. 5 shows expression verification results of a gE protein of the PRV-AgE strain.

(2) The experimental results are shown in FIG. 5. The results showed that compared with the wild-type strain, the expression of gE protein was not detected in the mutated gE gene, indicating that mutating the start codon could effectively inhibit the expression of gE protein.

(3) The above results showed that using the NG-ABE base editor to mutate the start codon of the gene could inhibit the expression of gE in the virus, thereby achieving better gene silencing effects.

The above embodiments are merely illustrative of some implementations of the present disclosure, and the description thereof is specific and detailed, but should not be construed as limiting the patent scope of the present disclosure. Corresponding changes and variations may be made by those skilled in the art according to the technical solutions and concepts described above, and all these changes and variations should fall within the protection scope of the claims of the present disclosure.

What is claimed is:

1. A gE protein-deleted pseudorabies virus (PRV) strain, the gE protein-deleted PRV strain being deposited in the China Center for Type Culture Collection (CCTCC) with a deposit number of CCTCC NO: V202323; and the gE protein-deleted PRV strain being constructed using an adenine base editor (ABE); (ABE) and wherein the gE protein-deleted PRV strain is constructed using a process comprising:

(1), constructing an sgRNA backbone plasmid, comprising:

designing an sgRNA sequence having the sequence set forth in SEQ ID NO: 2, using the ABE with a start codon of the gE gene in a PRV as a target site, synthesizing two single-stranded oligonucleotides according to the sgRNA sequence, annealing the single-stranded oligonucleotides to obtain a double-stranded DNA fragment with sticky ends, digesting a vector with a restriction endonuclease and recovering a resulting enzyme-digested fragment, and then ligating the enzyme-digested fragment to the double-stranded DNA fragment with sticky ends to obtain a ligation product, namely an sgRNA expression vector; wherein the single-stranded oligonucleotide has the sequences set forth in SEQ ID NO: 3 or SEQ ID NO: 4:

NG-ABE8e-gE-F: CACCGGCCGCATGGTCT-CAACCCC (SEQ ID NO: 3);
NG-ABE8e-gE-R: AAACGGGGTTGAGAC-CATGCGGCC (SEQ ID NO: 4);

the vector has the sequence set forth in SEQ ID NO: 11; the restriction endonuclease is a BbsI enzyme; and transforming the ligation product into a competent cell to allow plate screening and culture, selecting a resulting positive bacterial strain to allow expanded culture, and extracting a resulting plasmid from a resulting positive bacterial solution; and (2), transfection of the plasmid, comprising:

introducing the plasmid into a Vero81 cell, culturing the Vero81 cell to logarithmic growth phase at 37° C. and 5% (v/v) $CO_2$, collecting a resulting virus liquid, and centrifuging the virus liquid to collect a resulting supernatant;

wherein the adenine base editor is NG-ABE8e; and wherein a base at position 2 of a start codon in the gE gene of wild-type PRV is mutated from T to C to obtain a resulting mutated gE gene; wherein the resulting mutated gE gene is set forth in SEQ ID NO: 1.

2. A method for constructing the gE protein-deleted PRV strain according to claim 1 using an ABE, comprising the following steps:

(1), constructing an sgRNA backbone plasmid, comprising:

designing an sgRNA sequence having the sequence set forth in SEQ ID NO: 2, using the ABE with a start codon of the gE gene in a PRV as a target site, synthesizing two single-stranded oligonucleotides according to the sgRNA sequence, annealing the single-stranded oligonucleotide to obtain a double-stranded DNA fragment with sticky ends, digesting a vector with a restriction endonuclease and recovering a resulting enzyme-digested fragment, and then ligating the enzyme-digested fragment to the double-stranded DNA fragment with sticky ends to obtain a ligation product, namely an sgRNA expression vector; wherein the single-stranded oligonucleotide has the sequences set forth in SEQ ID NO: 3 or SEO ID NO: 4:

NG-ABE8e-gE-F: CACCGGCCGCATGGTCT-CAACCCC (SEO ID NO: 3);

NG-ABE8e-gE-R: AAACGGGGTTGAGAC-CATGCGGCC (SEO ID NO: 4);

the vector has the sequence set forth in SEO ID NO: 11;

the restriction endonuclease is a BbsI enzyme; and transforming the ligation product into a competent cell to allow plate screening and culture, selecting a resulting positive bacterial strain to allow expanded culture, and extracting a resulting plasmid from a resulting positive bacterial solution; and (2), transfection of the plasmid, comprising:

introducing the plasmid into a Vero81 cell, culturing the Vero81 cell to logarithmic growth phase at 37° C. and 5% (v/v) $CO_2$, collecting a resulting virus liquid, and centrifuging the virus liquid to collect a resulting supernatant.

3. The method according to claim 2, wherein the restriction endonuclease is a BbsI enzyme.

4. The method according to claim 2, wherein the Vero81 cell is cultured in a fetal bovine serum (FBS)-containing medium to a logarithmic growth phase before the transfection is conducted.

* * * * *

SEQUENCE LISTING

```
Sequence total quantity: 16
SEQ ID NO: 1             moltype = DNA  length = 1737
FEATURE                  Location/Qualifiers
misc_feature             1..1737
                         note = sequence of mutated gE gene encoding wild-type PRV
source                   1..1737
                         mol_type = other DNA
                         organism = synthetic construct
SEQUENCE: 1
acgcggccct ttctgctgcg cgccgcgcag ctcctggcgc tgctggccct ggcgctctcc  60
accgaggccc cgagcctctc cgccgagacg accccgggcc ccgtcaccga ggtcccgagt 120
ccctcggccg aggtctggga cgacctctcc accgaggccg acgacgatga cctcaacggc 180
gacctcgacg gcgacgaccg ccgcgcgggc ttcggctcgg ccctcgcatc cctgagggag 240
gcgccccgg cccatctggt gaacgtgtcc gagggcgcca acttcaccct cgacgcgcgc 300
ggcgacggcg ccgtgctggc cgggatctgg acgttcctgc ccgtccgcgg ctgcgacgcc 360
gtgtccggtga ccacggtgtg cttcgagacc gcgtgccacc cggacctggt gctgggccgc 420
gcctgcgtcc ccgaggcccc ggagatgggc atcggcgact acctgccgcc cgaggtgccg 480
cggctccggc gcgagccgcc catcgtcacc ccggagcggt ggtcgccgca cctgagcgtc 540
ctgcgggcca cgcccaacga cacgggcctc tacacgctgc acgacgcctc ggggccgcgg 600
gccgtgttct ttgtggcggt gggcgaccgg ccgcccgcgc cggcggaccc ggtgggcccc 660
gcgcgccacg agccccgctt ccacgcgctc ggcttccact cgcagctctt ctcgcccggg 720
```

```
gacacgttcg acctgatgcc gcgcgtggtc tcggacatgg gcgactcgcg cgagaacttt   780
accgccacgc tggactggta ctacgcgcgc gcgcccccgc ggtgcctgct gtactacgtg   840
tacgagccct gcatctacca cccgcgcgcg cccgagtgcc tgcgcccggt ggacccggcg   900
tgcagcttca cctcgccggc gcgcgcgcgg ctggtggcgc gccgcgcgta cgcctcgtgc   960
agcccgctgc tcggggaccg gtggctgacc gcctgccccc tcgacgccct cggcgaggag  1020
gtgcacacga acgccaccgc ggacgagtcg gggctgtacg tgctcgtgat gacccacaac  1080
ggccacgtcg ccacctggga ctacacgctc gtcgccaccg cggccgagta cgtcacggtc  1140
atcaaggagc tgacgccccc ggcccggggcc ccgggcaccc cgtggggccc cggcggcggc  1200
gacgacgcga tctacgtgga cggcgtcacg acgccggcgc cgcccgcgcg cccgtggaac  1260
ccgtacggcc ggacgacgcc cgggcgctg tttgtgctgg cgctgggctc cttcgtgatg  1320
acgtgcgtcg tcgggggggc catctggctc tgccgtgctgt gctcccggcg ccgggcggcc  1380
tcgcggccgt tccgggtgcc gacgcgggcg cggacgcaca tgctctctcc ggtgtacacc  1440
agcctgccca cgcacgagga ctactacggc gacgacgacg acgacgagga ggcgggcgtc  1500
atccgccggc gggccgcctc ccccagcgga gacgcgggct gcagggggcc gtacgcgagc  1560
ctggaccccg aggacgagtt cagcagcgac gaggacgacg ggctgtacgt gcgccccgag  1620
gaggcgcccc gctccggctt cgacgtctgg ttccgcgatc cggagaaacc ggaagtgacg  1680
aatggaccca actatggcgt gaccgccaac cgcctgttga tgtcccgccc cgcttaa     1737
```

SEQ ID NO: 2          moltype = DNA  length = 20
FEATURE                Location/Qualifiers
misc_feature        1..20
                      note = sgRNA sequence
source                 1..20
                      mol_type = other DNA
                      organism = synthetic construct
SEQUENCE: 2
ggccgcatgg tctcaacccc                                                              20

SEQ ID NO: 3          moltype = DNA  length = 24
FEATURE                Location/Qualifiers
misc_feature        1..24
                      note = forward sequence of single-stranded oligonucleotide
                      NG-ABE8e-gE-F
source                 1..24
                      mol_type = other DNA
                      organism = synthetic construct
SEQUENCE: 3
caccggccgc atggtctcaa cccc                                                   24

SEQ ID NO: 4          moltype = DNA  length = 24
FEATURE                Location/Qualifiers
misc_feature        1..24
                      note = reverse sequence of single-stranded oligonucleotide
                      NG-ABE8e-gE-R
source                 1..24
                      mol_type = other DNA
                      organism = synthetic construct
SEQUENCE: 4
aaacggggtt gagaccatgc ggcc                                                   24

SEQ ID NO: 5          moltype = DNA  length = 19
FEATURE                Location/Qualifiers
misc_feature        1..19
                      note = sequence of forwar primer gE-T-F for PCR detection
source                 1..19
                      mol_type = other DNA
                      organism = synthetic construct
SEQUENCE: 5
tgatcttcct gggcgggat                                                               19

SEQ ID NO: 6          moltype = DNA  length = 19
FEATURE                Location/Qualifiers
misc_feature        1..19
                      note = sequence of reversxe primer gE-T-R for PCR detection
source                 1..19
                      mol_type = other DNA
                      organism = synthetic construct
SEQUENCE: 6
tcggacacgt tcaccagat                                                              19

SEQ ID NO: 7          moltype = DNA  length = 26
FEATURE                Location/Qualifiers
source                 1..26
                      mol_type = other DNA
                      note = Original virus (WT-PRV)
                      organism = synthetic construct
SEQUENCE: 7
gtaccggcgt cgatgatgat ggtggc                                             26

| | | |
|---|---|---|
| SEQ ID NO: 8 | moltype = DNA  length = 26 | |
| FEATURE | Location/Qualifiers | |
| source | 1..26 | |
| | mol_type = other DNA | |
| | note = Edit NG-ABE8e gene | |
| | organism = synthetic construct | |
| SEQUENCE: 8 | | |
| gtaccggcgt cgacgatgat ggtggc | | 26 |
| | | |
| SEQ ID NO: 9 | moltype = DNA  length = 28 | |
| FEATURE | Location/Qualifiers | |
| source | 1..28 | |
| | mol_type = other DNA | |
| | note = NG-ABE8e gene of original virus | |
| | organism = synthetic construct | |
| SEQUENCE: 9 | | |
| gggttgagac catgcggccc tttctgct | | 28 |
| | | |
| SEQ ID NO: 10 | moltype = DNA  length = 28 | |
| FEATURE | Location/Qualifiers | |
| source | 1..28 | |
| | mol_type = other DNA | |
| | note = NG-ABE8e gene of edit virus | |
| | organism = synthetic construct | |
| SEQUENCE: 10 | | |
| gggttgagac cacgcggccc tttctgct | | 28 |
| | | |
| SEQ ID NO: 11 | moltype = DNA  length = 5610 | |
| FEATURE | Location/Qualifiers | |
| source | 1..5610 | |
| | mol_type = other DNA | |
| | note = vector pU6-sgRNA-Puro-2A-EGFP | |
| | organism = synthetic construct | |

SEQUENCE: 11
```
gagggcctat ttcccatgat tccttcatat ttgcatatac gatacaaggc tgttagagag   60
ataattggaa ttaatttgac tgtaaacaca agatattag tacaaaatac gtgacgtaga  120
aagtaataat ttcttgggta gtttgcagtt ttaaaattat gttttaaaat ggactatcat  180
atgcttaccg taacttcgaa gtatttcgat ttcttggctt tatatatctt gtggaaagga  240
cgaaacaccg ggtcttcgag aagacctgtt ttagagctag aaatagcaag ttaaaataag  300
gctagtccgt tatcaacttg aaaaagtggc accgagtcgg tgctttttttg tttttagagct  360
agaaatagca agttaaaata aggctagtcc gttttttagcg cgtgcgccaa ttctgcagac  420
aaatggctct agaggtaccc gttacataac ttacggtaaa tggcccgcct ggctgaccgc  480
ccaacgaccc ccgcccattg acgtcaatag taacgccaat agggactttc cattgacgtc  540
aatgggtgga gtatttacgg taaactgccc acttggcagt acatcaagtg tatcatatgc  600
caagtacgcc ccctattgac gtcaatgacg gtaaatggcc cgcctggcat tgtgcccagt  660
acatgacctt atgggacttt cctacttggc agtacatcta cgtattagtc atcgctatta  720
ccatgtcga ggtgagcccc acgttctgct tcactctccc catctccccc ccctccccac  780
ccccaatttt gtatttatttt attttttaat tattttgtgc agcgatgggg gcggggggg  840
gggggggggcg cgcgccaggc ggggcgggc ggggcgaggg gcggcgggg gcgaggcgga  900
gaggtgcggc ggcagccaat cagagcgcg cgctccgaaa gttccttttt atggcgaggc  960
ggcggcggcg gcggccctat aaaaagcgaa gcgcgccggcg ggcggagtc gctgcgcgct 1020
gccttcgccc cgtgccccgc tccgccgccg cctcgcgccg ccgcccggg ctctgactga 1080
ccgcgttact cccacaggtg agcgggcggg acggccctc tcctccgggc tgtaattagc 1140
tgagcaagag gtaagggttt aagggatggt tggtttgtgg gtattaatg tttaattacc 1200
tggacacct gcctgaaat cttttttttc aggttgacc ggtgccacca tggtgagcaa 1260
gggcgaggag ctgttcaccg gggtggtgcc catcctggtc gagctggacg gcgacgtaaa 1320
cggccacaag ttcagcgtgt ccggcgaggg cgagggcgat gccacctacg gcaagctgac 1380
cctgaagttc atctgcacca ccggcaagct gcccgtgccc tggcccaccc tcgtgaccac 1440
cctgacctac ggcgtgcagt gcttcagccg ctaccccgac cacatgaagc agcacgactt 1500
cttcaagtcc gccatgcccg aaggctacgt ccaggagcgc accatcttct tcaaggacga 1560
cggcaactac aagacccgcg ccgaggtgaa gttcgagggc gacaccctgg tgaaccgcat 1620
cgagctgaag ggcatcgact tcaaggagga cggcaacatc ctggggcaca gctggagta 1680
caactacaac agccacaacg tctatatcat ggccgacaag cagaagaacg gcatcaaggt 1740
gaacttcaag atccgccaca acatcgagga cggcagcgtg cagctcgccg accactacca 1800
gcagaacacc cccatcggcg acggccccgt gctgctgccc gacaaccact acctgagcac 1860
ccagtccgcc ctgagcaaag accccaacga aagcgcgat cacatggtcc tgctggagtt 1920
cgtgaccgcc gccgggatca ctctcggcat ggacgagctg tacaaggaat cggcagtgg 1980
agagggcaga ggaagtctgc taacatgcgg tgacgtcgag gagaatcctg gcccaatgac 2040
cgagtacaag cccacggtgc gcctcgcaca gtcccaggc gctacgccat 2100
cctcgccgcc gcgttcgccg actacccccg cacgcgccac accgtcgatc cggaccgcca 2160
catcgagcgg gtcaccgagc tgcaagaact cttcctcacg cgcgtcgggc tcgacatcgg 2220
caaggtgtgg gtcgcggacg acggcgccgc ggtggcggtc tggaccacgc cggagagcgt 2280
cgaagcgggg gcggtgttcg ccgagatcgg cccgcgcatg gccgagttga gcggttcccg 2340
gctgctcacg cagcaacaga tggaaggcct cctggcgccg caccggaccca aggagccgct 2400
gtggttcctg gccaccgtcg gagtctcgcc cgaccaccag gcaagggtc tgggcagcgc 2460
cgtcgtgctc cccggagtgg aggcggccga gcgcgccggg gtgcccgcct tcctggagac 2520
ctccgcgccc cgcaacctcc ccttctacga gcgggctcggc ttcaccgtca ccgccgacgt 2580
cgaggtgccc gaaggaccgc gcacctggtg catgacccgc aagcccggtg cctgagagct 2640
cgctgatcag cctcgactgt gccttctagt tgccagccat ctgttgttg ccctcccccc 2700
```

```
gtgccttcct tgaccctgga aggtgccact cccactgtcc tttcctaata aaatgaggaa  2760
attgcatcgc attgtctgag taggtgtcat tctattctgg ggggtggggt ggggcaggac  2820
agcaaggggg aggattggga agagaatagc aggcatgctg gggagcggcc gcaggaaccc  2880
ctagtgatgg agttggccac tccctctctg cgcgctcgct cgctcactga ggccgggcga  2940
ccaaaggtcg cccgacgccc gggctttgcc cgggcgcgct cagtgagcga gcgagcgcgc  3000
agctgcctgc aggggcgcct gatgcgcgta tttctcctta cgcatctgtg cggtatttca  3060
caccgcatac gtcaaagcaa ccatagtacg cgccctgtag cggcgcatta agcgcggcgg  3120
gtgtggtggt tacgcgcagc gtgaccgcta cacttgccag cgccttagcg cccgctcctt  3180
tcgctttctt cccttccttt ctcgccacgt tcgccggctt tccccgtcaa gctctaaatc  3240
ggggctccc tttagggttc cgatttagtg ctttacggca cctcgacccc aaaaaacttg  3300
atttgggtga tggttcacgt agtgggccat cgccctgata cggttttt cgcccttga  3360
cgttggagtc cacgttcttt aatagtggac tcttgttcca aactggaaca acactcaact  3420
ctatctcggg ctattctttt gatttataag ggattttgcc gatttcggtc tattggttaa  3480
aaaatgagct gatttaacaa aaatttaacg cgaattttaa caaatatta acgtttacaa  3540
ttttatggtg cactctcagt acaatctgct ctgatgccgc atagttaagc cagccccgac  3600
acccgccaac acccgctgac gcgccctgac gggcttgtct gctcccggca tccgcttaca  3660
gacaagctgt gaccgtctcc gggagctgca tgtgtcagag gttttcaccg tcatcaccga  3720
aacgcgcgag acgaaagggc ctcgtgatac gcctatttt ataggttaat gtcatgataa  3780
taatggtttc ttagacgtca ggtggcactt ttcggggaaa tgtgcgcgga acccctattt  3840
gtttattttt ctaaatacat tcaaatatgt atccgctcat gagacaataa ccctgataaa  3900
tgcttcaata atattgaaaa aggaagagta tgagtattca actttccgt gtcgcccta  3960
ttcccttttt tgcggcattt tgccttcctg ttttgctca cccagaaacg ctggtgaaag  4020
taaaagatgc tgaagatcag ttgggtgcac gagtgggtta catcgaactg gatctcaaca  4080
gcggtaagat ccttgagagt tttcgccccg aagaacgttt tccaatgatg agcacttta  4140
aagttctgct atgtggcgcg gtattatccc gtattgacgc cgggcaagag caactcggtc  4200
gccgcataca ctattctcag aatgacttgg ttgagtactc accagtcaca gaaaagcatc  4260
ttacggatgg catgacagta agagaattat gcagtgctgc cataaccatg agtgataaca  4320
ctgcggccaa cttactctg acaacgatcg gaggaccgaa ggagctaacc gcttttttgc  4380
acaacatggg gatcatgta actcgccttg atcgttggga accggagctg aatgaagcca  4440
taccaaacga cgagcgtgac accacgatgc ctgtagcaat ggcaacaacg ttgcgcaaac  4500
tattaactgg cgaactactt actctagctt cccggcaaca attaatagac tggatggagg  4560
cggataaagt tgcaggacca cttgctgct cggcccttcc ggctggctgg tttattgctg  4620
ataaatctgg agccggtgag cgtggaagcc gcggtatcat tgcagcactg ggccagatg  4680
gtaagccctc ccgtatcgta gttatctaca cgacggggag tcaggcaact atggatgaac  4740
gaaatagaca gatcgctgag ataggtgcct cactgattaa gcattggtaa ctgtcagacc  4800
aagtttactc atatatactt tagattgatt taaaacttca ttttaatt aaaaggatct  4860
aggtgaagat cctttttgat aatctcatga ccaaatccc ttaacgtgag ttttcgttcc  4920
actgagcgtc agacccgta gaaaagatca aaggatcttc ttgagatcct ttttttctgc  4980
gcgtaatctg ctgcttgcaa acaaaaaaac caccgctacc agcggtggtt tgtttgccgg  5040
atcaagagct accaactctt tttccgaagg taactggctt cagcagagcg cagataccaa  5100
atactgttct tctagtgtag ccgtagttag gccaccactt caagaactct gtagcaccgc  5160
ctacatacct cgctctgcta atcctgttac cagtggctgc tgccagtggc gataagtcgt  5220
gtcttaccgg gttggactca agacgatagt taccggataa aggcgcagcg gtcgggctga  5280
cgggggttc gtgcacacag cccagcttgg agcgaacgac ctacaccgaa ctgagatacc  5340
tacagcgtga gctatgagaa agcgccacgc ttcccgaagg gagaaaggcg gacaggtatc  5400
cggtaagcgg cagggtcgga acaggagagc gcacgaggga gcttcaggg gaaacgcct  5460
ggtatcttta gtgtcctgtc gggtttcgcc acctctgact tgagcgtcga ttttttgtgat  5520
gctcgtcagg ggggcggagc ctatggaaaa acgccagcaa cgcggccttt ttacggttcc  5580
tggccttttg ctggcctttt gctcacatgt                                    5610

SEQ ID NO: 12        moltype = DNA   length = 241
FEATURE              Location/Qualifiers
source               1..241
                     mol_type = other DNA
                     note = promoter U6
                     organism = Homo sapiens
SEQUENCE: 12
gagggcctat ttcccatgat tccttcatat ttgcatatac gatacaaggc tgttagagag   60
ataattggaa ttaatttgac tgtaaacaca aagatattac aaaaatac gtgacgtaga  120
aagtaataat ttcttgggta gtttgcagtt ttaaaattat gttttaaaat ggactatcat  180
atgcttaccg taacttgaaa gtatttcgat ttcttggctt tatatatctt gtggaaagga  240
c                                                                  241

SEQ ID NO: 13        moltype = DNA   length = 124
FEATURE              Location/Qualifiers
source               1..124
                     mol_type = other DNA
                     note = sgRNA scaffold
                     organism = synthetic construct
SEQUENCE: 13
gttttagagc tagaaatagc aagttaaaat aaggctagtc cgttatcaac ttgaaaaagt   60
ggcaccgagt cggtgctttt tgttttaga gctagaaata gcaagttaaa ataaggctag  120
tccg                                                               124

SEQ ID NO: 14        moltype = DNA   length = 717
FEATURE              Location/Qualifiers
source               1..717
                     mol_type = other DNA
                     note = EGFP
```

```
                    organism = synthetic construct
SEQUENCE: 14
atggtgagca agggcgagga gctgttcacc ggggtggtgc ccatcctggt cgagctggac  60
ggcgacgtaa acgccacaa gttcagcgtg tccggcgagg gcgagggcga tgccacctac  120
ggcaagctga ccctgaagtt catctgcacc accggcaagc tgcccgtgcc ctggcccacc  180
ctcgtgacca ccctgaccta cggcgtgcag tgcttcagcc gctacccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaag     717

SEQ ID NO: 15         moltype = DNA  length = 54
FEATURE               Location/Qualifiers
source                1..54
                      mol_type = other DNA
                      note = linker 2A
                      organism = Thosea asigna virus
SEQUENCE: 15
gagggcagag gaagtctgct aacatgcggt gacgtcgagg agaatcctgg ccca          54

SEQ ID NO: 16         moltype = DNA  length = 600
FEATURE               Location/Qualifiers
source                1..600
                      mol_type = other DNA
                      note = puromycin
                      organism = Streptomyces alboniger
SEQUENCE: 16
atgaccgagt acaagcccac ggtgcgcctc gccacccgcg acgacgtccc cagggccgta  60
cgcaccctcg ccgccgcgtt cgccgactac cccgccacgc gccacaccgt cgatccggac  120
cgccacatcg agcgggtcac cgagctgcaa gaactcttcc tcacgcgcgt cgggctcgac  180
atcggcaagg tgtgggtcgc ggacgacggc gccgcggtgg cggtctggac cacgccggag  240
agcgtcgaag cgggggcggt gttcgccgag atcggcccgc gcatggccga gttgagcggt  300
tcccggctgg ccgcgcagca acagatgaa ggcctcctgg cgccgcaccg gcccaaggag  360
cccgcgtggt tcctggccac cgtcggagtc tcgcccgacc accagggcaa gggtctgggc  420
agcgccgtcg tgctcccgg agtgagggcg gccgagcgcg ccggggtgcc cgccttcctg  480
gagacctccg cgcccgcaa cctcccctc tacgagcggc tcggcttcac cgtcaccgcc  540
gacgtcgagg tgcccgaagg accgcgcacc tggtgcatga cccgcaagcc cggtgcctga  600
```